US00PP31464P3

(12) United States Plant Patent
Chandra et al.

(10) Patent No.: US PP31,464 P3
(45) Date of Patent: Feb. 18, 2020

(54) ZOYSIAGRASS NAMED 'KSUZ 0802'

(50) Latin Name: ***Zoysia matrella* x *Zoysia japonica* $F_1$ hybrid**
Varietal Denomination: KSUZ 0802

(71) Applicants: The Texas A&M University System, College Station, TX (US); Kansas State University Research Foundation, Manhattan, KS (US)

(72) Inventors: Ambika Chandra, Dallas, TX (US); Milton C. Engelke, College Station, TX (US); Anthony D. Genovesi, Dallas, TX (US); Jack Fry, College Station, TX (US)

(73) Assignees: The Texas A&M University System, College Station, TX (US); Kansas State University Research Foundation, Manhattan, KS (US)

( * ) Notice: Subject to any disclaimer, the term of this patent is extended or adjusted under 35 U.S.C. 154(b) by 0 days.

(21) Appl. No.: 15/932,850

(22) Filed: May 7, 2018

(65) Prior Publication Data

US 2019/0343031 P1 Nov. 7, 2019

(51) Int. Cl.
*A01H 5/12* (2018.01)
*A01H 6/46* (2018.01)

(52) U.S. Cl.
USPC ..... Plt./390
CPC ..... *A01H 6/469* (2018.05)

(58) Field of Classification Search
USPC ..... Plt./390
See application file for complete search history.

(56) References Cited

U.S. PATENT DOCUMENTS

| | | | |
|---|---|---|---|
| PP10,778 | P | 2/1999 | Engelke |
| PP14,130 | P2 | 9/2003 | Engelke et al. |
| 2018/0352713 | P1 | 12/2018 | Engelke |

OTHER PUBLICATIONS

Fry, J. and Chandra, A. "Release of KSUZ 0802 Zoysiagrass," Kansas Agricultural Station Research Reports, vol. 2, Issue 4, (2016).*
Chandra, et al., "Registration of 'KSUZ 0802' Zoysiagrass," Journal of Plant Registrations, 11(2):100-106, 2017.
Chandra, et al., "Release of KSUZ 0802 Zoysiagrass," Resilience Emerging From Scarcity and Abundance Meeting, Phoenix, AZ, Nov. 8, 2016. Available at <https://scisoc.confex.com/crops/2016am/webprogram/Paper99564.html>, accessed on Feb. 21, 2019.
Fry and Chandra, "Release of KSUZ 0802 Zoysiagrass," Kansas Agricultural Experiment Station Research Reports, vol. 2, Issue 4, (2016).
Fry and Chandra, "New Fine-Textured, Cold-Hardy Zoysiagrass on the Horizon," TURFNews, The Kansas Turfgrass Foundation Newsletter, Manhattan, KS 2015.
"Sod Solutions to Roll Out Innovation *Zoysia,*" SportsTurf (2018). Available at <https://sportsturfonline.com/2018/02/15/sod-solutions-to-roll-out-innovation-zoysia/>, accessed on Feb. 21, 2019.
"Texas Scientists Breed New Heartier Turf," Fox4News, Dallas-Fort worth (2018). Available at <http://www.fox4news.com/good-day/texas-scientists-breed-new-heartier-turf>, accessed on Feb. 21, 2019.

* cited by examiner

*Primary Examiner* — Susan McCormick Ewoldt
(74) *Attorney, Agent, or Firm* — Dentons US LLP

(57) ABSTRACT

The new and distinct zoysiagrass variety described herein is a *Z. matrella* x *Z. japonica* $F_1$ hybrid named 'KSUZ 0802'. 'KSUZ 0802' can be distinguished by its superior turf quality, fine-textured leaves, increased resistance to bluegrass billbug (*Sphenophorus parvulus* Ghyllenhaal), and cold tolerance that is comparable to zoysiagrass varieties adapted to the transition zone growing region in the U.S.

5 Drawing Sheets

Latin name of the genus and species of the plant claimed: *Zoysia matrella* x *Zoysia japonica* $F_1$ hybrid.

Variety denomination: 'KSUZ 0802'.

BACKGROUND OF THE INVENTION

Zoysiagrass (*Zoysia* spp.) is one of the most versatile warm-season turfgrasses and is used on lawns, landscapes, and golf courses. The *Zoysia* genus is indigenous to Pacific Rim countries with a geographic distribution extending from 42° N to 42° S, and displays a wide range of genetic variability that includes 11 different species. Most zoysiagrasses are tetraploid (2n=4x=40); however, there are diploid *Zoysia matrella* (L.) Merr. accessions (2n=2x=20). The species within the *Zoysia* genus are cross compatible, which makes interspecific hybridization feasible. *Zoysia* spp. possess good tolerance to heat, shade, and salt, and require minimal nutrition and mowing. Some zoysiagrass cultivars, particularly within *Z. japonica*, also exhibit good freezing tolerance.

The following *Zoysia* species are recognized as turfgrasses in the U.S.: *Z. japonica* Steud. (Japanese lawngrass), *Z. matrella* (L.) Merr. (Manilagrass), and *Z. pacifica* (Goudsw.) M. Hotta and Kuroki (Mascarenegrass). Zoysiagrass is best adapted and widely used in the southern and southeastern regions of the U.S., and limited freezing tolerance is the primary factor hindering widespread implementation of zoysiagrass in other regions, including the region referred to as the "transition zone." The center of this transition zone runs from eastern New Mexico to northern Virginia. Since 1952, *Zoysia japonica* cultivar 'Meyer' (unpatented) has been the predominant cultivar used in this transition zone because of its excellent freezing tolerance. Also, the *Zoysia japonica* cultivar 'DALZ 0102' (U.S. application Ser. No. 15/731,369), which has been recently released, exhibits a freezing tolerance that is comparable or slightly poorer than that of 'Meyer', but the rate of establishment, turf quality, growth under shade, and tolerance to pests displayed by 'DALZ 0102' are all superior to that displayed by 'Meyer'.

Both 'Meyer' and 'DALZ 0102' exhibit medium-coarse to coarse leaf texture that is suitable for lawns and golf course fairways; however, the finer leaf texture of *Zoysia matrella* cultivars, such as, 'Cavalier' (U.S. Pat. No. PP10,778) and 'Zorro' (U.S. Pat. No. PP14,130), is preferable. Nonetheless, *Zoysia matrella* cultivars display poor to moderate freezing tolerance and limited adaptation to the transition zone.

SUMMARY OF THE INVENTION

The present disclosure relates to a new and distinct variety of zoysiagrass named 'KSUZ 0802'. 'KSUZ 0802', formerly tested as TAES 5311-26, is an $F_1$ interspecific hybrid derived in 2001 from a cross between the *Zoysia matrella* (L). Merr. cultivar 'Cavalier' used as a female parent and an ecotype of *Z. japonica* Steud. 'Anderson 1' (unpatented) used as the male pollen donor. The cross was performed in 2001 in Dallas, Tex. by controlled hand pollination. Receptive protogynous flowers were pollinated with pollen that was collected from the male parent in a glycine shoot bag, and the identity of these pollinated flowers was maintained by placing a bamboo skewer next to the pollinated inflorescences and covering them with a microcentrifuge tube. These pollinated flowers were allowed to mature for six weeks before the seed was harvested.

The harvested seeds were processed by dissecting the hulls away from the caryopsis. In vitro seed germination was accomplished by surface sterilizing the naked caryopses in a 50% bleach solution that was followed by three washes with sterile, deionized water. The hard seed coat of zoysiagrass also required that each seed be scarified with a scalpel blade to accelerate germination on a half strength MS medium. The resulting 610 progeny from 17 different families were transferred and planted in a spaced plant nursery in Manhattan, Kans. in 2004 and evaluated for turf quality and winter survival. The top 31 hybrids were propagated in Manhattan, Kans. in 2006 and 2007 in a greenhouse to plant a field trial to evaluate the performance of these hybrids under golf course fairway management. In 2008, 7 out of these 31 hybrids, including 'KSUZ 0802', were advanced to multi-location testing in the transition zone based on their freezing tolerance and overall quality. 'KSUZ 0802' was first asexually propagated in Manhattan, Kans. in 2006 via transplanting vegetative plugs.

The new and distinct variety 'KSUZ 0802' disclosed herein is well suited for use on golf course fairways and tees, home lawns, and other recreational areas in the transition zone. 'KSUZ 0802' can be distinguished at least by its freezing tolerance, spring green-up, fall color retention, finer leaf texture, superior turf quality, and resistance to bluegrass billbug (*Sphenophorus parvulus* Ghyllenhaal) damage. 'KSUZ 0802' can be distinguished from its female parent ('Cavalier') at least by cold hardiness; and 'KSUZ 0802' can be distinguished from its male parent ('Anderson 1') at least by leaf texture. 'Cavalier' is fine-textured with poor cold hardiness; 'Anderson 1' is cold hardy and coarse textured; and 'KSUZ 0802' is cold hardy and fine-textured.

The following are the most outstanding and distinguishing characteristics of 'KSUZ 0802': (1) 'KSUZ 0802' exhibits freezing tolerance similar to the transition zone adapted cultivars 'Meyer' and 'DALZ 0102'; (2) 'KSUZ 0802' exhibits superior turf quality relative to transition zone adapted cultivars 'Meyer' and 'DALZ 0102'; (3) 'KSUZ 0802' exhibits finer leaf texture relative to transition zone adapted cultivars 'Meyer' and 'DALZ 0102'; and (4) 'KSUZ 0802' exhibits increased resistance to bluegrass billbug damage relative to transition zone adapted cultivar 'Meyer'. Further, a multi-location, multi-year field evaluation has demonstrated that the overall performance of 'KSUZ 0802' is superior to that of either 'Meyer' and 'DALZ 0102'. 'KSUZ 0802' achieved "78" out of a possible turf performance index (TPI) score of "86"; whereas, 'Meyer' and 'DALZ 0102' achieved a "52" and "57," respectively.

BRIEF DESCRIPTION OF THE DRAWINGS

'KSUZ 0802' is illustrated by the accompanying photographs, which show typical stolon, leaf blade, and inflorescence of the claimed plant. The colors shown are as true as can be reasonably obtained by conventional photographic procedures.

DETAILED BOTANICAL DESCRIPTION

Figure 1:
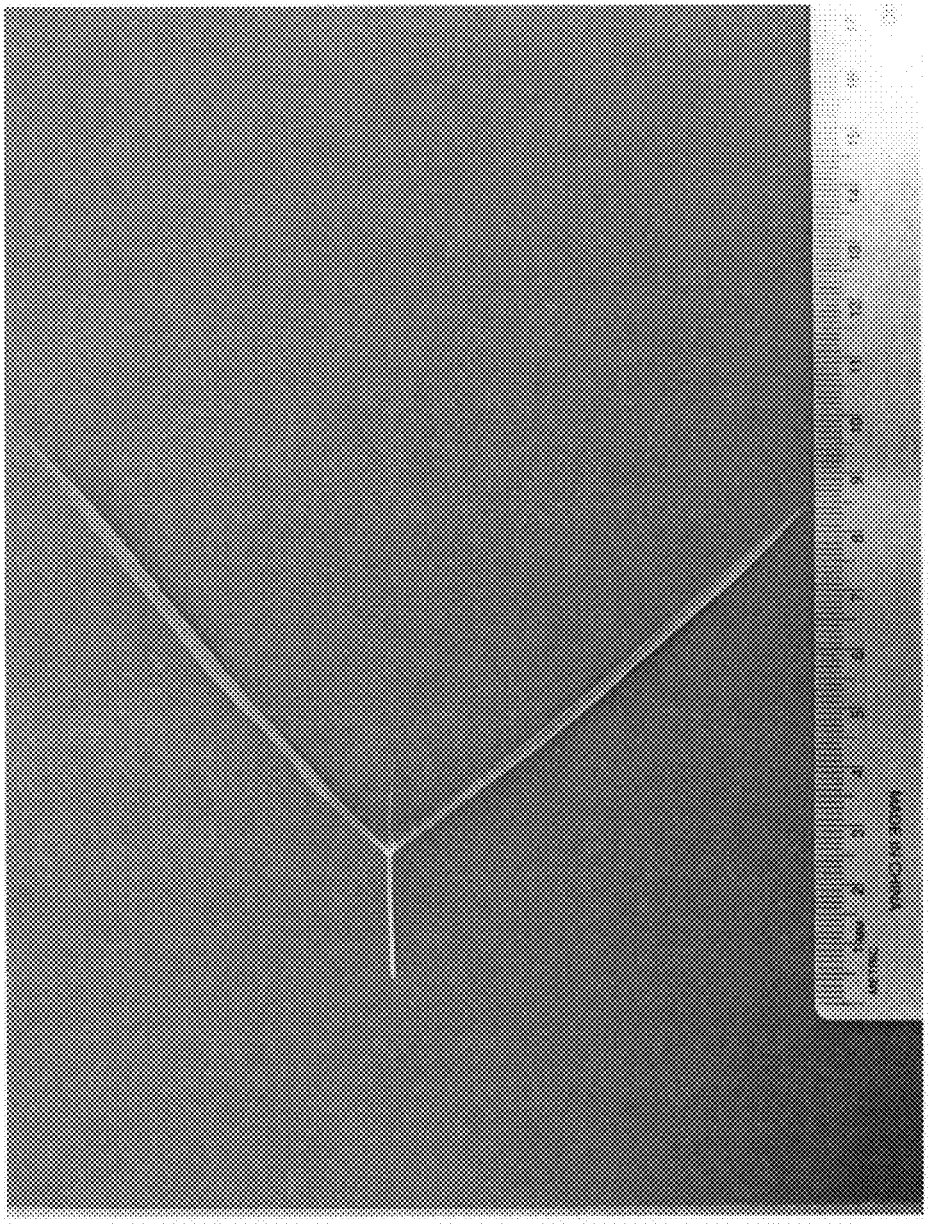
FIG. 1—Shows leaf blades of 'KSUZ 0802'.
Figure 2:
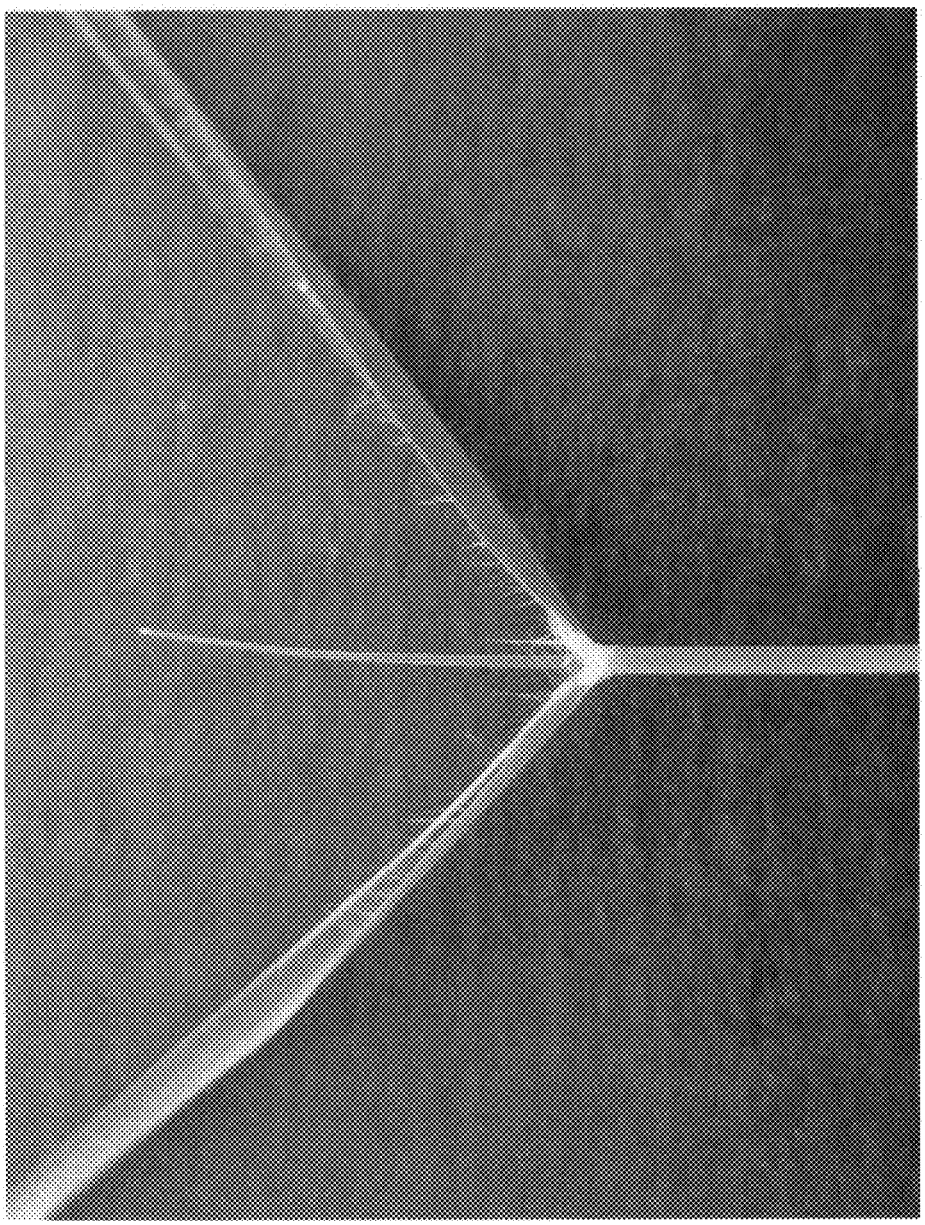
FIG. 2—Shows the leaf hair of 'KSUZ 0802'.
Figure 3:
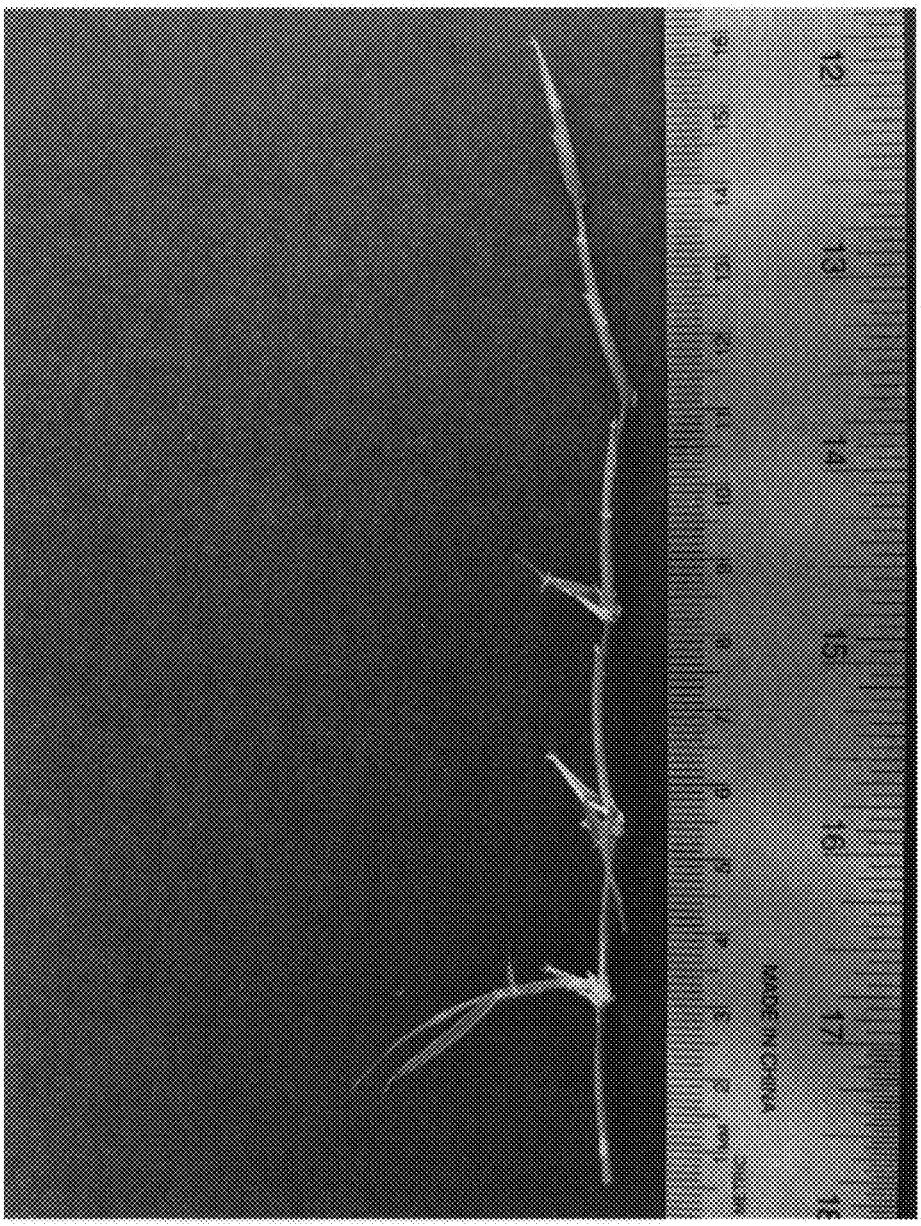
FIG. 3—Shows stolons of 'KSUZ 0802'.
Figure 4:
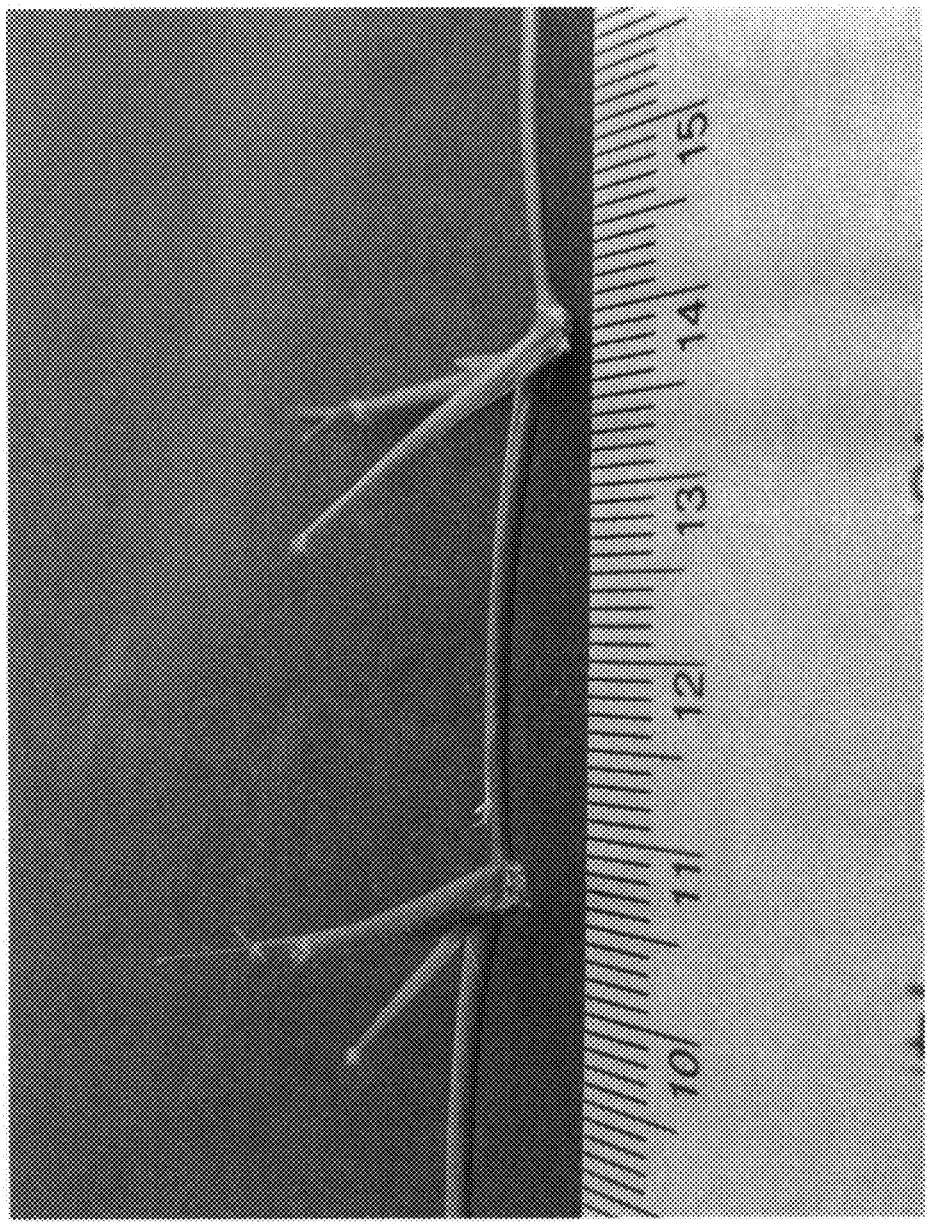
FIG. 4—Shows the stolon thickness of 'KSUZ 0802'.
Figure 5:
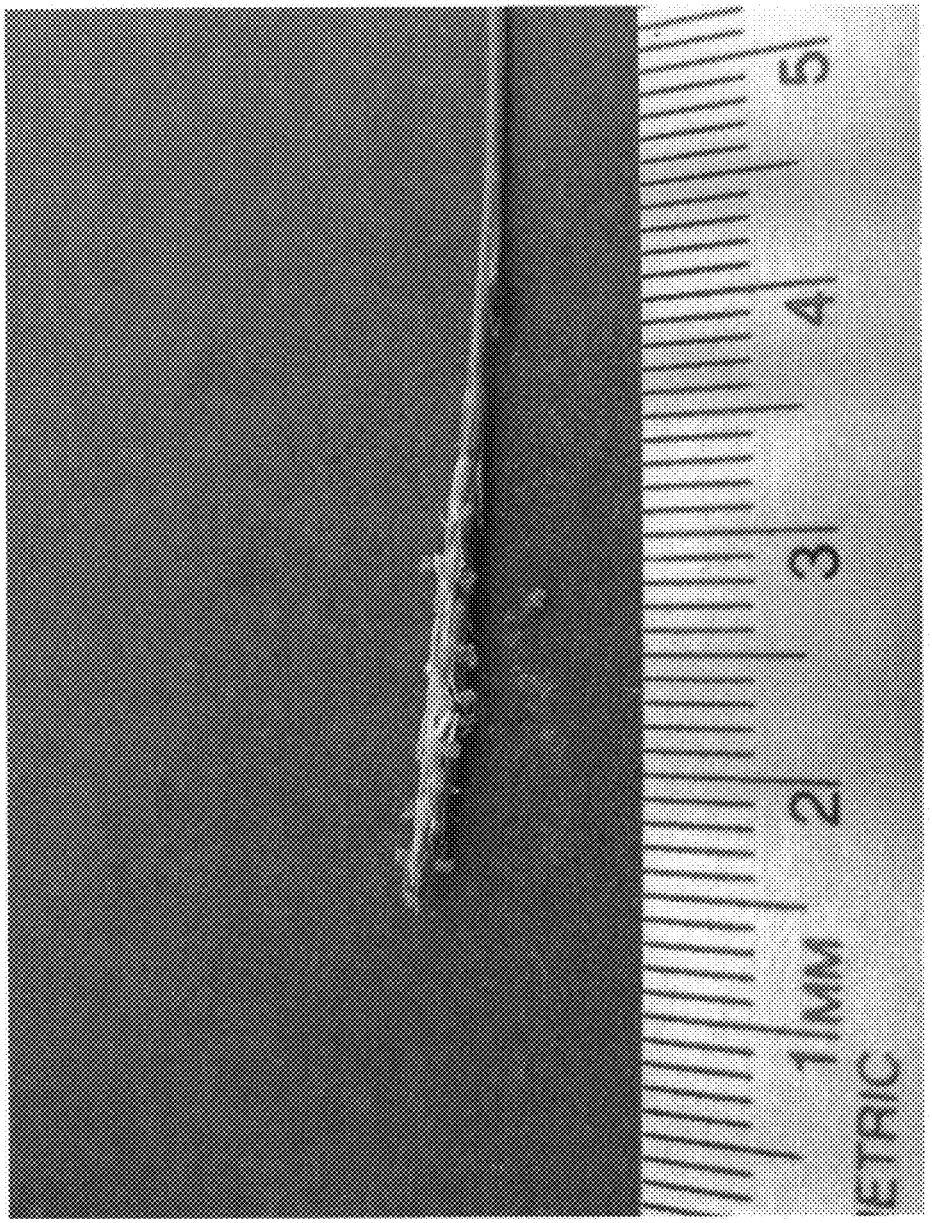
FIG. 5—Shows an inflorescence of 'KSUZ 0802'.

The following detailed description sets forth the distinctive characteristics of *Z. matrella* x *Z. japonica* $F_1$ hybrid 'KSUZ 0802'. Color references are to The RHS Colour Chart of The Royal Horticultural Society of London (RHS), 2007 5th Edition. Version 2, unless otherwise indicated. RHS color designations provided refer to both mature and immature stages. If any RHS color designations below differ from the accompanying photographs, the RHS color designations are accurate.

Leaf blades:
- *Length.*—96.5 mm.
- *Width.*—2.9 mm.
- *Shape.*—linear, blade rolled in bud, flat surface.
- *Apex.*—pointed.
- *Aspect.*—concave.
- *Margin.*—smooth.
- *Adaxial surface.*—Texture: moderate trichromes. Color: RHS 131C; turquoise-green.
- *Abaxial surface.*—Texture: smooth. Color: RHS 131B; turquoise-green.
- *Venation.*—Pattern: parallel. Color: RHS 131B; turquoise-green.

Flag leaf length: 8.0 mm.
Inflorescence:
- *Type.*—spike.
- *Length.*—24.7 mm.
- *Width.*—1.8 mm.

Glumes: present.
Lemmas: present.
Awns: absent.
Time of flowering: Late spring to early summer.
Seed: present.

Culm length: 46 mm.

Stolons:

*Internode length.*—22.3 mm.

*Internode color.*—RHS 130; turquoise-green.

*Internode diameter.*—1.4 mm.

*Node diameter.*—2.8 mm.

*Node color.*—RHS 61A; purple-violet.

Morphological Analysis of 'KSUZ 0802': 'KSUZ 0802' was morphologically compared to 'DALZ 0102', 'Emerald' (unpatented), 'Meyer', and 'Zorro'. Plant material was propagated into 27.3 cm-diameter×24.1 cm-deep pots filled with SUNSHINE® VP mix and 5% sand (v:v). Three replicate pots of each cultivar received PETERS PROFESSIONAL® fertilizer (20 N−20 $P_2O_5$−20 $K_2O$) monthly during establishment. Plant material was grown in a greenhouse that was maintained at 26/18° C. day/night temperature, and 70% humidity from October, 2014 through March, 2015. Pots were watered three to four times per week as needed. All potted material was moved outside of the greenhouse in April, 2015 to promote growth under natural sunlight and ambient temperature. Leaf tissue was hand-trimmed weekly during the growing season and stolons were allowed to drape around pots. Digital calipers were used to collect data for all traits. Data were collected on Jan. 14, 2015 and Mar. 31, 2015 using plants maintained in the greenhouse. Leaf width was measured on Jun. 23, 2015 after the plants were moved outside. Color ratings were determined on non-cloudy days using the Munsell Color Chart for Plant Tissues, 1977 Edition. A maximum of twelve samples from three replicate pots were measured for each trait for each cultivar. Internode length and diameter were measured between the fourth and fifth nodes of the longest stolon. Stolon node diameter was measured from the fourth node. The third youngest leaf was measured for leaf blade length and leaf width 15 mm above the collar. Flag leaf length was measured from the collar to the tip of the leaf. Inflorescence length was measured from the top of the peduncle to the tip of the raceme. Data were analyzed using the PROC GLM model in SAS® 9.3. Means were separated using Fisher's protected LSD ($P \geq 0.05$).

Morphological Comparison of 'KSUZ 0802' to Commercial Varieties:

Stolon:

*Internodes.*—Those of 'KSUZ 0802' were longer than those of 'DALZ 0102', 'Emerald', and 'Meyer', and similar to those of 'Zorro' (Table 1).

*Internode diameter.*—That of 'KSUZ 0802' was narrower than that of 'DALZ 0102', similar to that of 'Meyer', and wider than that of 'Emerald' and 'Zorro' (Table 1).

*Node diameter.*—That of 'KSUZ 0802' was similar to that of 'DALZ 0102' and 'Meyer', and wider than that of 'Emerald' and 'Zorro' (Table 1).

Leaf blade:

*Lengths.*—Those of 'KSUZ 0802' were shorter than those of 'Meyer', similar to those of 'Emerald' and 'Zorro', and longer than those of 'DALZ 0102' (Table 1).

*Widths.*—Those of 'KSUZ 0802' were finer than those of 'DALZ 0102' and 'Meyer', and coarser than those of 'Emerald' and 'Zorro' (Table 1).

Flag leaf lengths: Those of 'KSUZ 0802' were longer than those of 'Emerald' and 'Zorro', and similar to that of 'Meyer' (Table 1).

Inflorescence lengths: Those of 'KSUZ 0802' were shorter than those of 'Meyer', longer than those of 'Zorro', and similar to those of 'DALZ 0102' and 'Emerald' (Table 1).

TABLE 1

Morphological comparison of 'KSUZ 0802' and commercial zoysiagrass cultivars.

| | Stolon internode length (mm) | Stolon internode diameter (mm) | Stolon node diameter (mm) | Leaf blade length (mm) |
|---|---|---|---|---|
| 'KSUZ 0802' | 22.3 a | 1.4 b | 2.8 a | 96.5 b |
| 'DALZ 0102' | 16.4 c | 1.8 a | 2.8 a | 73.6 c |
| 'Emerald' | 16.2 c | 1.2 c | 2.1 b | 107.0 b |
| 'Meyer' | 18.2 bc | 1.5 b | 2.7 a | 169.5 a |
| 'Zorro' | 21.2 ab | 1.2 c | 2.3 b | 104.5 b |

| | Leaf blade width (mm) | Flag leaf length (mm) | Inflorescence length (mm) |
|---|---|---|---|
| 'KSUZ 0802' | 2.9 c | 8.0 a | 24.7 b |
| 'DALZ 0102' | 3.7 a | — | 25.5 b |
| 'Emerald' | 2.0 d | 3.6 bc | 22.9 b |
| 'Meyer' | 3.4 b | 5.6 ab | 41.0 a |
| 'Zorro' | 1.8 d | 1.8 c | 19.4 c |

Means within a column followed by the same letter are not significantly different at $P \leq 0.05$.

'KSUZ 0802' establishment and stolon growth evaluation: Vegetative plugs of 'KSUZ 0802', 'Meyer', and 'DALZ 0102' were planted in June, 2007 and June, 2008 at Manhattan, Kans. and evaluated for stolon growth characteristics and establishment rates. In 2007, 'KSUZ 0802' exhibited a greater stolon initiation rate (5.0/week) than 'Meyer' (2.9/week) and 'DALZ 0102' (2.6/week); however, all three varieties exhibited similar rates in 2008. All three varieties exhibited similar stolon branching rates in 2007; whereas, 'Meyer' and 'DALZ 0102' both exhibited higher stolon branching rates than 'KSUZ 0802' in 2008. All three varieties displayed similar stolon elongation rates in both 2007 and 2008. In both years, the plugs planted in June for all three varieties each achieved the same level of plot coverage by September. *Z. japonica* lines generally display faster establishment rates, as well as aggressive growth and re-growth characteristics when compared with *Z. matrella* lines. 'KSUZ 0802' a finer textured, *Z. matrella* x *Z. japonica* $F_1$ hybrid line therefore unexpectedly exhibited similar stolon growth characteristics and establishment rates as 'Meyer' and 'DALZ 0102', which are both *Z. japonica* lines.

'KSUZ 0802' freezing tolerance evaluation: The freezing tolerance of 'KSUZ 0802', 'Meyer', and 'DALZ 0102' were compared in 2007 and 2008. Grass cores measuring 6 cm in diameter were randomly collected from plots at Manhattan, Kans. that were maintained under a cultural regimen similar to golf course fairways. The sampled cores were subjected to controlled freezing temperatures (−6 to −22° C.) in a cold stress simulator during midwinter. The lethal temperature resulting in death of 50% of grass tillers ($LT_{50}$) of 'KSUZ 0802' was statistically similar to that of 'Meyer' and 'DALZ 0102' in both 2007 and 2008.

'KSUZ 0802' multi-state progeny evaluation: 'KSUZ 0802', 'Meyer', and 'DALZ 0102' were planted together in the summer of 2009 at all locations except Manhattan, Kans., where they were planted in the summer of 2008, and Fletcher and Jackson Springs, N.C., where they were planted in the summer of 2010. Data from Wichita, Kans. (KS1); Columbia, Mo. (MO); Stillwater, Okla. (OK); Knoxville, Tenn. (TN); Dallas, Tex. (TX); Virginia Beach, Va. (VA1); and Blacksburg, Va. (VA2) were collected from 2009 to 2012. Data from Manhattan, Kans. (KS2) were collected from 2008 to 2011, and data from Fletcher, N.C. (NC1) and Jackson Springs, N.C. (NC2) were collected from 2010 to 2012. The only field study location not within the transition zone was Dallas, Tex.. Experimental hybrids and checks were replicated three times in a randomized complete block design, and were established vegetatively from 7.6 cm×7.6 cm plugs. For each replication, six plugs were quartered and planted equidistant in the centermost 1.5 m×1.5 m of 2.1 m×2.1 m plots. Irrigation (2.5 cm) was applied to supplement rainfall each week during the first season to promote establishment; and thereafter, to prevent dormancy. Nitrogen was applied at 25 kg/ha during each growing month in the first year, but did not exceed a total of 100 kg/ha in the years after establishment. Actively growing plots were mowed weekly at 9 out of 10 locations to achieve a 3.8 to 6.4 cm cutting height that is recommended for home lawn management. Grasses in the evaluations conducted in Manhattan, Kans. and Stillwater, Okla. were mowed 2 to 3 days per week to maintain a height of 1.3 cm, which is suggested height for fairways. Oxadiazon at 146.5 kg/ha was applied as a preemergence herbicide immediately after planting plugs to control annual summer weeds. Establishment was rated as a percentage of plot cover, with data collected during the first growing season at all 9 evaluated locations (Table 2). Turf quality was rated monthly based on color, density, texture, and uniformity from May to September on a scale from 1 to 9 in which "1" corresponds to "poorest quality" and "9" corresponds to "optimum quality" (Tables 3 and 8). Leaf texture was rated once each year on a scale from 1 to 9 in which "1" corresponds to "very coarse" and "9" corresponds to "very fine" (Tables 4 and 8). Genetic color, Spring green-up, and Fall color retention were rated once each year on a scale from 1 to 9 in which "1" corresponds to "brown/dead" and "9" corresponds to "dark green" (Tables 5-8). Bluegrass billbug (*S. parvulus* Ghyllenhal) damage was also assessed as a percentage of plot damage (Table 8). Frequency of data collection for each trait varied by location, and is described in the respective table footnotes. Data were analyzed using JMP® 10 software. Analysis of variance (ANOVA) was conducted separately for each individual location using cultivar, year, and cultivar×year interaction as fixed effects, and replications were nested within each year. If the cultivar×year interaction was not significant for an individual location, data were pooled across years and reanalyzed. Cultivar means were separated using Fisher's protected LSD (P≤0.05). In addition, a turfgrass performance index (TPI) for each cultivar was determined (Tables 2-8) by adding the number of times a cultivar appeared in the top statistical group ('a'), or in the case of the billbug damage evaluations the lowest grouping was considered superior.

TABLE 2

Establishment (% plot cover) of 'KSUZ 0802' and commercial zoysiagrass cultivars at nine locations maintained at lawn height (3.8 to 6.4 cm).

| | KS1 | MO | NC1 | NC2 | OK |
|---|---|---|---|---|---|
| 'KSUZ 0802' | 87.5 a | 79.7 ab | 55.0 a | 68.3 a | 71.0 a |
| 'DALZ 0102' | 86.7 a | 85.0 a | 51.7 a | 70.0 a | 79.0 a |
| 'Meyer' | 76.2 b | 76.0 b | 41.7 a | 45.0 a | 81.3 a |
| | TN | TX | VA1 | VA2 | TPI |
| 'KSUZ 0802' | 97.3 a | 73.3 a | 63.3 ab | 70.2 a | 9 |
| 'DALZ 0102' | 99.2 a | 70.0 a | 74.0 a | 74.4 a | 9 |
| 'Meyer' | 91.2 b | 73.3 a | 53.0 b | 67.1 a | 5 |

Means in a column followed by the same letter are not significantly different at P ≤ 0.05.

Means determined in 2010: KS1: (June-October); NC1: (October); NC2: (October); OK: (April, June-July, and September-October); TN: (June-August, September (twice), and October); VA1 (April-May and July-September); and VA2: (May-August). Means determined in 2009: MO (October-November). Means determined in 2012: TX (June).

TABLE 3

Turf quality of 'KSUZ 0802' and commercial zoysiagrass cultivars at nine locations maintained at lawn height (3.8 to 6.4 cm).

| | 2010 KS1 | 2011 KS1 | 2012 KS1 | MO | NC1 | NC2 | 2010 OK | 2011 OK | 2012 OK |
|---|---|---|---|---|---|---|---|---|---|
| 'KSUZ 0802' | 5.3 a | 5.6 a | 4.5 a | 6.1 a | 7.4 a | 5.7 a | 5.0 a | 7.1 a | 7.1 a |
| 'DALZ 0102' | 5.1 a | 5.2 a | 5.3 a | 6.2 a | 5.4 b | 5.4 ab | 5.1 a | 6.0 b | 6.0 b |
| 'Meyer' | 3.9 b | 5.2 a | 3.3 b | 5.3 a | 7.3 a | 5.0 b | 5.1 a | 6.1 b | 6.1 b |
| | TN | 2011 TX | 2012 TX | VA1 | 2010 VA2 | 2011 VA2 | 2012 VA2 | TPI | |
| 'KSUZ 0802' | 6.6 a | 4.6 b | 3.0 ab | 7.2 a | 5.7 a | 6.5 a | 6.2 a | 15 | |
| 'DALZ 0102' | 6.5 a | 5.5 a | 3.7 a | 6.9 a | 5.4 ab | 6.3 a | 5.6 b | 12 | |
| 'Meyer' | 6.5 a | 3.6 c | 2.3 b | 7.0 a | 4.7 b | 4.9 b | 5.1 b | 6 | |

Means in a column followed by the same letter are not significantly different at P ≤ 0.05. Years are presented separately for locations at which a significant cultivar × year interaction was observed.

Means were determined: KS1: 2010 (May-September), 2011 (May-September), and 2012 (May-September); MO: 2010 (May and July), 2011 (June), and 2012 (September); NC1: 2011 (June-September) and 2012 (May-October); NC2: 2011 (May-October) and 2012 (May-October); OK: 2010 (May and August-October), 2011 (May-October), and 2012 (April-July and October); TN: 2010 (July-August, September (twice), and October) and 2011 (May-June and August-September); TX: 2011 (May-October) and 2012 (May (twice) and June); VA1: 2010 (August-September), 2011 (May-October), and 2012 (May-October); and VA2: 2010 (July-August, September (twice), and October), 2011 (May-September), and 2012 (May-October).

TABLE 4

Leaf texture of 'KSUZ 0802' and commercial zoysiagrass cultivars at nine locations maintained at lawn height (3.8 to 6.4 cm).

| | KS1 | MO | 2010 NC1 | 2011 NC1 | 2012 NC1 | NC2 |
|---|---|---|---|---|---|---|
| 'KSUZ 0802' | 7.4 a | 6.0 a | 7.0 a | 8.0 a | 8.0 a | 6.9 a |
| 'DALZ 0102' | 5.2 b | 4.0 c | 5.7 b | 5.0 c | 5.7 b | 5.1 b |
| 'Meyer' | 5.7 b | 5.0 b | 7.0 a | 7.0 b | 7.7 a | 7.6 a |
| | OK | TN | TX | VA1 | VA2 | TPI |
| 'KSUZ 0802' | 6.7 a | 7.7 a | 6.0 a | 7.7 a | 6.7 a | 11 |
| 'DALZ 0102' | 2.0 b | 5.0 c | 4.7 c | 3.7 b | 3.3 c | 0 |
| 'Meyer' | 5.3 a | 6.7 b | 5.5 b | 6.7 a | 5.0 b | 5 |

Means in a column followed by the same letter are not significantly different at P ≤ 0.05. Years are presented separately for locations at which a significant cultivar × year interaction was observed.

Means were determined: KS1: 2010 (September), 2011 (July), and 2012 (July); MO: 2009 (October); NC1: 2010 (October), 2011 (August), and 2012 (July); NC2: 2010 (October), 2011 (July), and 2012 (July); OK: 2009 (September); TN: 2009 (September); TX: 2011 (May) and 2012 (May); VA1: 2010 (July); and VA2: 2010 (July).

TABLE 5

Genetic color of 'KSUZ 0802' and commercial zoysiagrass cultivars at nine locations maintained at lawn height (3.8 to 6.4 cm).

| | KS1 | MO | NC1 | NC2 | OK |
|---|---|---|---|---|---|
| 'KSUZ 0802' | 5.7 a | 7.3 a | 7.2 a | 5.8 a | 8.0 a |
| 'DALZ 0102' | 4.4 b | 5.8 b | 4.8 b | 5.5 a | 7.3 ab |
| 'Meyer' | 6.1 a | 7.3 a | 7.3 a | 6.7 a | 7.0 b |

| | TN | TX | VA1 | VA2 | TPI |
|---|---|---|---|---|---|
| 'KSUZ 0802' | 7.3 a | 7.0 a | 7.3 ab | 5.7 a | 9 |
| 'DALZ 0102' | 7.7 a | 7.0 a | 7.0 b | 6.0 a | 5 |
| 'Meyer' | 6.3 a | 7.7 a | 8.0 a | 4.3 a | 8 |

Means in a column followed by the same letter are not significantly different at P ≤ 0.05.

Means were determined: KS1: 2010 (September), 2011 (July), and 2012 (July); MO: 2011 (June) and 2012 (September); NC1: 2011 (August) and 2012 (July); NC2: 2011 (July) and 2012 (July); OK: 2009 (September); TN: 2009 (September); TX: 2011 (June); VA1: 2011 (July); and VA2: 2010 (July).

TABLE 6

Spring green-up of 'KSUZ 0802' and commercial zoysiagrass cultivars at nine locations maintained at lawn height (3.8 to 6.4 cm).

| Cultivar | 2010 KS1 | 2011 KS1 | 2012 KS1 | MO | NC1 | NC2 | OK |
|---|---|---|---|---|---|---|---|
| 'KSUZ 0802' | 4.3 a | 6.7 a | 5.3 a | 6.8 a | 7.8 a | 5.2 b | 2.8 a |
| 'DALZ 0102' | 4.3 a | 5.3 b | 3.7 b | 8.1 a | 7.7 a | 7.2 a | 3.0 a |
| 'Meyer' | 3.0 a | 7.3 a | 4.0 b | 6.8 a | 7.8 a | 6.7 a | 3.3 a |

| Cultivar | 2010 TN | 2011 TN | TX | VA1 | 2011 VA2 | 2012 VA2 | TPI |
|---|---|---|---|---|---|---|---|
| 'KSUZ 0802' | 6.3 a | 9.0 a | 4.0 a | 6.0 a | 5.0 a | 8.0 a | 12 |
| 'DALZ 0102' | 7.3 a | 9.0 a | 4.7 a | 5.8 a | 4.0 ab | 8.0 a | 11 |
| 'Meyer' | 6.2 a | 9.0 a | 4.7 a | 6.2 a | 2.7 b | 6.7 b | 10 |

Means in a column followed by the same letter are not significantly different at P ≤ 0.05. Years are presented separately for locations at which a significant cultivar × year interaction was observed.
Means were determined: KS1: 2010 (April), 2011 (April), and 2012 (May); MO: 2010 (April and May (twice)) and 2011 (June); NC1: 2011 (April) and 2012 (April); NC2: 2011 (April) and 2012 (March); OK: 2010 (March and April); TN: 2010 (April (twice)) and 2011 (April); TX: 2011 (March); VA1: 2010 (March), 2011 (April and March), and 2012 (March); and VA2: 2011 (April) and 2012 (April).

TABLE 7

Fall color retention of 'KSUZ 0802' and commercial zoysiagrass cultivars at six locations maintained at lawn height (3.8 to 6.4 cm).

| Cultivar | 2010 KS1 | 2012 KS1 | 2009 MO | 2010 MO | 2011 MO | NC1 |
|---|---|---|---|---|---|---|
| 'KSUZ 0802' | 3.7 b | 2.2 ab | 3.8 a | 5.5 a | 3.7 a | 7.0 a |
| 'DALZ 0102' | 5.7 a | 1.8 b | 4.3 a | 5.3 a | 4.3 a | 5.8 a |
| 'Meyer' | 4.0 b | 3.1 a | 3.0 a | 5.7 a | 4.7 a | 7.0 a |

| Cultivar | 2010 NC2 | 2011 NC2 | 2012 NC2 | OK | TX | TPI |
|---|---|---|---|---|---|---|
| 'KSUZ 0802' | 6.3 b | 3.8 b | 6.0 a | 4.3 a | 4.3a | 8 |
| 'DALZ 0102' | 6.0 b | 6.5 a | 7.3 a | 4.7 a | 5.0 a | 9 |
| 'Meyer' | 8.7 a | 5.0 ab | 7.3 a | 5.0 a | 3.7 a | 10 |

Means in a column followed by the same letter are not significantly different at P ≤ 0.05. Years are presented separately for locations at which a significant cultivar × year interaction was observed.
Means were determined: KS1: 2010 (October) and 2012 (October and November (twice)); MO: 2009 (October and November), 2010 (October (twice)), and 2011 (October); NC1: 2010 (October) and 2012 (October); NC2: 2010 (October), 2011 (October and November), and 2012 (October); OK: 2010 (October); and TX: 2011 (November).

TABLE 8

Performance of 'KSUZ 0802' and commercial cultivars at two locations mowed at fairway height (1.3 cm).

| | Turf quality | | | | | | |
|---|---|---|---|---|---|---|---|
| | 2008 KS2 | 2009 KS2 | 2010 KS2 | 2011 KS2 | 2010 OK | 2011 OK | 2012 OK |
| 'KSUZ 0802' | 8.0 a | 6.3 a | 7.1 a | 7.2 a | 5.4 a | 7.6 a | 6.6 a |
| 'DALZ 0102' | 6.0 b | 5.9 a | 6.5 a | 6.6 a | 4.9 a | 6.2 b | 6.1 b |
| 'Meyer' | 7.0 ab | 4.8 b | 5.5 b | 5.6 b | 5.0 a | 6.1 b | 5.6 c |

| | Leaf texture | | Genetic color | | | Spring green-up |
|---|---|---|---|---|---|---|
| | | | 2009 | 2010 | 2011 | |
| | KS2 | OK | OK | OK | OK | OK |
| 'KSUZ 0802' | 8.0 a | 7.3 a | 5.0 a | 4.0 a | 2.7 b | 3.7 b |
| 'DALZ 0102' | 5.0 c | 2.0 c | 4.8 a | 4.0 a | 4.0 a | 3.0 b |
| 'Meyer' | 6.3 b | 4.7 b | 5.3 a | 5.3 a | 4.0 a | 5.5 a |

| | Fall color retention | | Billbug damage | | |
|---|---|---|---|---|---|
| | | | 2009 | 2010 | |
| | KS2 | OK | KS2 | KS2 | TPI |
| 'KSUZ 0802' | 4.0 a | 5.7 a | 14.1 b | 2.8 b | 14 |
| 'DALZ 0102' | 4.6 a | 5.3 a | 0.0 c | 0.0 b | 11 |
| 'Meyer' | 4.1 a | 5.7 a | 31.7 a | 12.2 a | 8 |

Means in a column followed by the same letter are not significantly different at P ≤ 0.05. Years are presented separately for locations at which a significant cultivar × year interaction was observed.
Turf quality ratings means were determined: KS2: 2008 (September), 2009 (June-August), 2010 (May-September), and 2011 (May and July-September); and OK: 2010 (May, August, September, and October), 2011 (May-October), and 2012 (April-July, and October). Leaf texture means were determined: KS2: 2008 (September), 2009 (June), and 2011 (August); and OK: 2009 (September). Genetic color means were determined: KS2: 2009 (April and June), 2010 (April (twice)), and 2011 (April). Spring green-up means were determined: OK: 2010 (March-April). Fall color retention means were determined: KS2: 2008 (October and November), 2009 (October), 2010 (October), and 2011 (October); and OK: 2010 (October). Billbug damage means were determined: KS2: 2009 (July and August) and 2010 (June-September).

Traits and characteristics of 'KSUZ 0802' grown at home lawn height (grasses mowed weekly to achieve 3.8 to 6.4 cm cutting height)

*Establishment.*—'KSUZ 0802' establishment was similar to 'DALZ 0102' at all 9 locations; and 'KSUZ 0802' establishment was superior to 'Meyer' at 2 locations and similar to 'Meyer' at all other locations (Table 2). 'KSUZ 0802' and 'DALZ 0102' were in the statistically superior group at all 9 locations; whereas, 'Meyer' was only in the statistically superior group at 5 locations.

*Turf quality.*—'KSUZ 0802' turf quality was superior to that of 'DALZ 0102' in 4 of the 16 evaluations and only underperformed 'DALZ 0102' in 1 evaluation; and 'KSUZ 0802' turf quality was superior to that of 'Meyer' in 9 of the 16 evaluations and never underperformed 'Meyer' (Table 3). 'KSUZ 0802' was in the statistically superior group in 15 of the 16 evaluations; whereas, 'DALZ 0102' and 'Meyer' were only in the statistically superior group in 12 and 6 of those 16 evaluations, respectively.

*Leaf texture.*—'KSUZ 0802' leaf texture was significantly finer than that of 'DALZ 0102' in all 11 evaluations; and 'KSUZ 0802' leaf texture was significantly finer than that of 'Meyer' in 6 of the 11 evaluations and never underperformed 'Meyer' (Table 4). 'KSUZ 0802' was in the statistically superior group in all 11 evaluations; whereas, 'DALZ 0102' and 'Meyer' were only in the statistically superior group in 0 and 5 of those 11 evaluations, respectively.

*Genetic color.*—'KSUZ 0802' genetic color was superior to that of 'DALZ 0102' at 3 of the 9 locations and never underperformed 'DALZ 0102'; and 'KSUZ 0802' genetic color was superior to that of 'Meyer' at one of the 9 locations and never underperformed 'Meyer' (Table 5). 'KSUZ 0802' was in the statistically superior group at all 9 locations; whereas, 'DALZ 0102' and 'Meyer' were only in the statistically superior group at 5 and 8 of those 9 locations, respectively.

*Spring green-up.*—'KSUZ 0802' Spring green-up was superior to that of 'DALZ 0102' in 2 of the 13 evaluations; 'KSUZ 0802' Spring green-up was superior to that of 'Meyer' in 3 of the 13 evaluations (Table 6). 'KSUZ 0802' only underperformed 'DALZ 0102' and 'Meyer' in the NC2 evaluation. 'KSUZ 0802' was in the statistically superior group in 12 of the 13 evaluations; whereas, 'DALZ 0102' and 'Meyer' were only in the statistically superior group in 11 and 10 of those 13 evaluations, respectively.

*Fall color retention.*—'KSUZ 0802' Fall color retention was similar to that of 'DALZ 0102' in 9 of the 11 evaluations and underperformed 'DALZ 0102' in only 2 evaluations; and 'KSUZ 0802' Fall color retention was similar to that of 'Meyer' in 10 of the 11 evaluations and underperformed 'Meyer' in only 1 evaluation (Table 7). 'KSUZ 0802' was in the statistically superior group in 8 of the 11 evaluations; whereas, 'DALZ 0102' and 'Meyer' were in the statistically superior group in 9 and 10 of those 11 evaluations, respectively. Fall color retention is a desirable trait extending the green appearance of the turf stand into the autumn season; however, early Fall dormancy and the associated loss of green color (low Fall color retention ratings) has been shown to be directly related to increased freezing tolerance.

Traits and characteristics of 'KSUZ 0802' grown at golf course fairway height (grasses mowed 2 to 3 days a week to achieve 1.3. cm cutting height)

*Turf quality.*—'KSUZ 0802' turf quality was superior to that of 'DALZ 0102' in 3 of the 7 evaluations and never underperformed 'DALZ 0102'; 'KSUZ 0802' turf quality was superior to that of 'Meyer' in 5 of the 7 evaluations and never underperformed 'Meyer' (Table 8). 'KSUZ 0802' was in the statistically superior group in all 7 evaluations; whereas, 'DALZ 0102' and 'Meyer' were only in the statistically superior group in 4 and 2 of those 7 evaluations, respectively.

*Leaf texture.*—'KSUZ 0802' leaf texture was significantly finer than that of 'DALZ 0102' and 'Meyer' at both locations (Table 8). 'KSUZ 0802' was in the statistically superior group at both locations; whereas, 'DALZ 0102' and 'Meyer' were never in the statistically superior group.

*Genetic color.*—'KSUZ 0802' genetic color was similar to that of 'DALZ 0102' and 'Meyer' in 2 of the 3 evaluations and underperformed both commercial varieties in the third evaluation (Table 8). 'KSUZ 0802' was in the statistically superior group in 2 of the 3 evaluations; whereas, 'DALZ 0102' and 'Meyer' were in the statistically superior group in all evaluations.

*Spring green-up.*—'KSUZ 0802' Spring green-up was similar to that of 'DALZ 0102' in the single evaluation; however 'KSUZ 0802' underperformed 'Meyer' in that evaluation (Table 8). 'Meyer' was the only variety in the statistically superior group in this evaluation.

*Fall color retention.*—'KSUZ 0802' Fall color retention was similar to that of 'DALZ 0102' and 'Meyer' at both locations (Table 8). All three varieties were in the statistically superior group at both locations.

*Bluegrass Billbug* (*Sphenophorus parvulus Ghyllenhaal*) *damage.*—'Meyer' is susceptible to bluegrass billbug damage; whereas, 'DALZ 0102' exhibits excellent resistance. 'KSUZ 0802' resistance to bluegrass billbug damage was superior to that of 'Meyer' in both evaluations; whereas, 'KSUZ 0802' resistance to bluegrass billbug damage was similar to 'DALZ 0102' in 1 evaluation and underperformed 'DALZ 0102' in the other evaluation (Table 8). 'DALZ 0102' was in the statistically superior group in both evaluations; 'KSUZ 0802' was in the statistically superior group in only one evaluation; and 'Meyer' was never in a statistically superior group in these evaluations.

What is claimed is:

1. A new and distinct variety of zoysiagrass called 'KSUZ 0802' as shown and described herein.

* * * * *